(12) United States Patent
Zhang et al.

(10) Patent No.: US 8,765,695 B2
(45) Date of Patent: Jul. 1, 2014

(54) USE OF GINSENOSIDE RG1, ITS METABOLITES GINSENOSIDE RH1 AND/OR PPT

(75) Inventors: Juntian Zhang, Beijing (CN); Shifeng Chu, Beijing (CN)

(73) Assignees: Jecui Health Industry Corp. Ltd., Yunnan (CN); Institute of Materia Medica, Chinese Academy of Medical Sciences, Yunnan (CN)

( * ) Notice: Subject to any disclaimer, the term of this patent is extended or adjusted under 35 U.S.C. 154(b) by 115 days.

(21) Appl. No.: 12/530,970

(22) PCT Filed: Dec. 25, 2007

(86) PCT No.: PCT/CN2007/003776
§ 371 (c)(1),
(2), (4) Date: Mar. 8, 2010

(87) PCT Pub. No.: WO2008/110050
PCT Pub. Date: Sep. 18, 2008

(65) Prior Publication Data
US 2011/0034403 A1 Feb. 10, 2011

(51) Int. Cl.
*C07J 41/00* (2006.01)
*A01N 45/00* (2006.01)

(52) U.S. Cl.
USPC .................................................. 514/26; 536/5

(58) Field of Classification Search
None
See application file for complete search history.

(56) References Cited

U.S. PATENT DOCUMENTS 6,444,237 B1 9/2002 Heleen
7,759,101 B2 * 7/2010 Jin et al. ................ 435/200

FOREIGN PATENT DOCUMENTS

| CN | 1425382 A | 6/2003 |
|---|---|---|
| CN | 1732963 A | 2/2006 |
| CN | 1795868 A | 7/2006 |
| DE | 101 58 281 A1 * | 5/2003 |
| KR | 10-2005-0108274 | 11/2005 |
| WO | 2006/001654 A | 1/2006 |

OTHER PUBLICATIONS

Yoshimura et al., "Preventive effects of various ginseng saponins on the development of copulatory disorder induced by prolonged individual housing in male", Methods and Findings in Experimental and Clinical Pharmacology, Prous, Barcelona, ES, vol. 20, No. 1, Jan. 1, 1998, pp. 59-64.
European Search Report—EP 07 84 6012—mailed on Feb. 22, 2010.
"Testicular Damage in Rat", Journal of Chongqing Medical University, Mar. 2007, vol. 32, No. 3, pp. 236-238. Hao et al.
Wang Y, Liu T.H., Wang W., et al. "Studies on the Metabolism of Ginsenoside Rg1 by Intestinal Bacteria and its Absorbed Metabolites in Rat and Human Sera", ACTA Pharmaceutica Sinica, Apr. 2000, vol. 35, No. 4, pp. 284-288.
International Search Report—PCT/CN2007/003776—mailed on Apr. 3, 2008.
Andrew S. Crimmel, Chad S. Conner, and Manoj Monga, "Withered Yang: A Review of Traditional Chinese Medical Treatment of Male Infertility and Erectile Dysfunction", Journal of Andrology, vol. 22, No. 2, (Mar./Apr. 2001), pp. 173-182.
Canadian Office Action for CA 2,680,560, mailed Oct. 12, 2012.
David R.J. Glenn, M.R.C.O.G., Carmel M. McVicar, Ph.D., Neil McClure, F.R.C.O.G., and Sheena E.M. Lewis, Ph.D., "Sildenafil citrate improves sperm motility but causes a premature acrosome reaction in vitro", Fertility and Sterility, vol. 87, No. 5, (May 2007), pp. 1064-1070.
European Communication for EP 07 846 012.8-2123, mailed Oct. 12, 2012.
European Communication for EP 07 846 012.8-2123, mailed Sep. 29, 2011.
Hao, J., Wang Y.X., HE, J.L., et al."Ginsenoside Rg1 Protect against Cadmium-induced Tesicular Damage in Rat", Journal of Chongqing Medical University. V. 32, No. 3; (Mar. 2007); pp. 236-238.
Rok Keber, Damjana Rozman, Simon Horvat, "Sterols in spermatogenesis and sperm maturation", Journal of Lipid Research (www.jlr.org) (Oct. 2012), pp. 1-32.
Singh Rajender, Pandey Rahul, Abbas Ali Mahdi, "Mitochondria, spermatogenesis and male infertility", Mitochondrion 10, (2010), pp. 419-428.
Xiaoying Wang, Ph.D., Shifeng Chu, MD., Tianxiu Qian, Ph.D., Ji Chen, MS, and Juntian Zhang, MD., "Ginsenoside Rg1 Improves Male Copulatory Behavior Via Nitric Oxide/Cyclic Guanosine Monophosphate Pathway", J. Sex Med, V. 7; (2010); pp. 743-750.
Japanese Office Action for JP 2009-552987, mailed Oct. 26, 2012.
Park, Jeong Sook et al., "The Therapeutic Effect of Tissue Cultured Root and Wild Panax ginseng C.A. Mayer on Spermatogenetic Disorder" *Archives of Pharmacal Research*, vol. 29, No. 9, (2006); pp. 800-807.
Canadian Office Action for CA 2,680,560, mailed Sep. 25, 2013.
Seock-Yeon Hwang et al., "Panax ginseng improves survival and sperm quality in guinea pigs exposed to 2,3,7,8-tetrachlorodibenzo-p-dioxin," BJU International, 94/4, pp. 663-668, Aug. 2004.
A. Mkrtchyan et al., "A phase I clinical study of *Andrographis paniculata* fixed combination Kan Jang versus ginseng and valerian on the semen quality of healthy male subjects," Phytomedicine, 12, pp. 403-409, Jun. 2005.

* cited by examiner

*Primary Examiner* — Lawrence E Crane
(74) *Attorney, Agent, or Firm* — Brinks Gilson & Lione

(57) ABSTRACT

The present invention relates to use of an active ingredient selected from ginsenoside Rg1, its metabolites ginsenoside Rh1 and Ppt for preparing a medicament and a health care product for improving sexual function of male mammals, and for providing the effect of spermatogenesis. The present invention further relates to a pharmaceutical composition for improving sexual function of male mammals, and/or for providing the effect of spermatogenesis, which comprises at least one active ingredient selected from ginsenoside Rg1, its metabolites ginsenoside Rh1 and Ppt, and a pharmaceutically acceptable excipient.

18 Claims, No Drawings

USE OF GINSENOSIDE RG1, ITS METABOLITES GINSENOSIDE RH1 AND/OR PPT

TECHNICAL FIELD

The present invention relates to the use of an active ingredient selected from ginsenoside Rg1, its metabolites ginsenoside Rh1 and Ppt for preparing a medicament and a health care product for improving sexual function of male mammals, for preparing a medicament with the effect of spermatogenesis, in particular for preparing a medicament and a health care product for promoting spermatogenesis, and increasing number and/or quality of sperms. The present invention further relates to a pharmaceutical composition and a health care product for improving sexual function of male mammals, and/or for providing the effect of spermatogenesis, in particular for promoting spermatogenesis, and increasing number and/or quality of sperms, which comprise at least one active ingredient selected from ginsenoside Rg1, its metabolites ginsenoside Rh1 and Ppt, and a pharmaceutically acceptable excipient.

BACKGROUND ART

According to statistic, among couples of child-bearing age all over the world, the rate of sterility is about 15%, and about 40% of the factors causing the sterility are attributed to the husband's side. Since the $20^{th}$ century, the fertility of male obviously tends to decrease all over the world due to environmental pollution, spreading of social disease and AIDS, excessive smoking and drug addiction, abuse of hormones medicament, and etc.

On the one side, the study in epidemiology demonstrates that, among men of above 20 ages in USA, the incidence rate of erectile dysfunction is 18.4%. If calculated according to the statistic of census made in 2000, the number of men who suffer from this disease in USA shall be in the order of 18 millions. The incidence rate of this disease is closely relevant to age, varying from 5.1% (men aged 20-39) to 70.2% (men aged above 70). As a whole, 65.0% of men can always have normal erection and fulfill coitus; 16.5% of men can have normal erection in general cases; 12.3% of men occasionally can have erection and fulfill coitus; and 6.2% of men never have normal erection. As a PDE5 inhibitor for oral administration, Sildenafil relieves the pain of up to millions of patients suffering from sexual dysfunction, but some side effects as subsequently resulted therefrom are also very serious.

On the other side, as reported, since 1940 to 1990, the number of sperms contained in per ml of semen of adults decreases from $1.13 \times 10^8$ to $6.6 \times 10^7$, and the amount of semen decreases from 3.40 ml to 2.75 ml. As compared with the situation in 1940, the sperm density of men all over the world decreases by 50%, i.e., decreases by 1% per annual in average. In addition to the decrease in number of sperms, the ratio of active sperms and the ratio of sperms in normal shape also decrease year after year (which decrease by 0.6% and 0.5% per annual, respectively). The continuous decrease in quality of semen directly leads to reduced fertility and reproductive function, which has gradually become an obvious social problem. One of crucial factors causing male sterility is the decrease in quality of sperms (number and motility of sperms), so it is very important to search for a medicament that can improve the quality of sperms. However, until now, there is still no medicament all over the world that has an exact therapeutic effect, and can increase the number of sperms and improve the activity of sperms.

Therefore, in reproductive medicine field, it has long been a difficult problem yet to be solved to develop a medicament capable of improving sexual function of male mammals, in particular men, increasing number of sperms, and improving quality of sperms.

In order to solve the above problem, the present inventors discovered upon a lot of researches that plant-derived ginsenoside Rg1, in particular its metabolites ginsenoside Rh1 and/or Ppt, can effectively improve sexual function of men, promote spermatogenesis, increase number of sperms, and improve quality of sperms.

SUMMARY OF INVENTION

As is well known, ginsenoside is one of main ingredients in ginseng. At present, at least 40 kinds of ginsenoside monomers have been isolated and extracted from ginseng plant, which may be generally divided into the following three categories in terms of their chemical structures: 20s-Protopanxadiol, 20s-Protopanxatriol and oleanolic acid. Ginsenoside Rg1 belongs to the category of 20s-Protopanxatriol, and converts into Rh1 and/or Ppt after metabolism, which are expressed in the following structure:

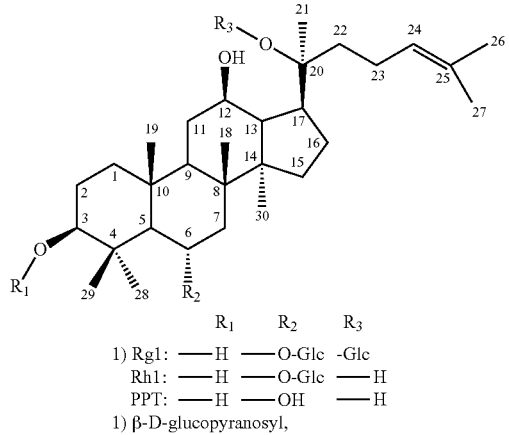

|  | $R_1$ | $R_2$ | $R_3$ |
|---|---|---|---|
| 1) Rg1: | —H | —O-Glc | -Glc |
| Rh1: | —H | —O-Glc | —H |
| PPT: | —H | —OH | —H |

1) β-D-glucopyranosyl,

In one aspect, the present invention relates to use of an active ingredient selected from ginsenoside Rg1, in particular its metabolites ginsenoside Rh1 and/or Ppt, for improving sexual function of male mammals.

In the present invention, the term "improving sexual function of male mammals" refers to increasing frequency of sexual behaviour and shortening latent period of sexual behaviour of males. In concrete, the action mechanism of improving sexual function of male mammals resides in increasing content of testosterone in serum of male mammals, and increasing content of cGMP in corpus cavernosum.

In another aspect, the present invention relates to use of an active ingredient selected from ginsenoside Rg1, its metabolites ginsenoside Rh1 and Ppt for preparing a medicament with the effect of spermatogenesis. In the present invention, the term "spermatogenesis" includes promoting spermatogenesis, increasing number of sperms, and/or improving quality of sperms.

In the present invention, the mammals are preferably human.

As is well known, gossypol contained in cottonseed oil is a toxic agent. It damages the spermatogenesis of testis tissue, thereby leading to reduced number of sperms, reduced survival rate of sperms, and reduced activity of sperms. The present inventors established aspermatogenesis model by using adult mice with administration of ip of gossypol acetate. The present inventors discovered that, at the same time of administering gossypol to mice, the administration of ginsenoside Rg1 by gavage at different doses could markedly alleviate the damage of gossypol on quality of sperms, and significantly increase number of sperms, increase survival rate of sperms, and improve motility of sperms.

The present inventors further studied a mechanism of ginsenoside Rg1 for promoting spermatogenesis. The sperm-damaging function of gossypol mainly includes interfering metamorphosis of spermatids and development of spermatocytes at middle-late stages, thereby leading to damage of sperms and atrophy of contorted seminiferous tubules. It was discovered by study that the damaging effect of gossypol on sperms was mainly due to that it generates excessive nitrous oxide (NO) in testis tissue. NO, as free radical, damages spermatogenic tissue and spermatids as well as interstitial cells, and thereby reduces the generation and release of testosterone (T). The present inventors tested by radioimmune assay the content of nitrous oxide (NO) in testis tissue, and the contents of testosterone (T), luteinizing hormone (LH) and follicle stimulating hormone (FSH) in serum. The test results demonstrated that Rg1 could markedly reduce excessive NO in testis tissue, to thereby protect sperms from the damage by NO, and increase the content of T in blood. Meanwhile, Rg1 exerted no notable influence on the contents of LH and FSH in blood ($P>0.05$).

After further study on the metabolites ginsenoside Rh1 and Ppt of ginsenoside Rg1, the present inventors surprisingly found that these metabolites per se also independently had the effect of improving sexual function and spermatogenesis of male mammals.

In another aspect, the present invention relates to a method for improving sexual function and/or spermatogenesis of male mammals, comprising administering to a subject a therapeutically effective amount of at least one active ingredient selected from ginsenoside Rg1, its metabolites ginsenoside Rh1 and Ppt.

The term "therapeutically effective amount" used herein refers to an amount that can produce the desired therapeutic effect, e.g., curing, preventing, inhibiting or at least partially inhibiting or partially preventing target disease or disorder, when administered to a specific subject according to the nature and severity of the subject's disease or disorder.

The therapeutically effective dose of the compound in the present invention is determined according to the data obtained from, e.g., cell incubation test and animal study, and can be used in the preparation of dose range useful for human and other mammals. The dose of the compound is preferably within the range that has the minimum toxicity or no toxicity and includes $ED_{50}$ in systemic plasma or other body fluid concentration. The dose may vary within this range, which depends on the dosage form used and the administration route. As for any compound in the present invention, its therapeutically effective dose may be estimated at the beginning according to animal test. The dose may be designed in an animal model, to thereby obtain the test range that includes $IC_{50}$ (i.e. the concentration of test compound that reaches a half of the maximum inhibition concentration) in systemic plasma concentration. This information can be utilized to more exactly determine the useable dose in human and other mammals. The plasma level of compound can be determined by, e.g., high performance liquid chromatography.

The amount of the compound that can form a single dosage form in combination with a pharmaceutically acceptable vehicle varies according to the subject under treatment and the concrete administration mode. As shall be understood by a person skilled in the art, the unit amount of compound contained in individual dose of each dosage form does not need to constitute a therapeutically effective amount by itself, because the therapeutically effective amount may be achieved by administering a plurality of individual doses. The choice of the dose depends on the dosage form used, the disease to be treated and the concrete purpose to be achieved as determined by a person skilled in the art.

In still another aspect, the present invention relates to a pharmaceutical composition for improving sexual function of male mammals, and/or for providing the effect of spermatogenesis, which comprises a therapeutically effective amount of at least one active ingredient selected from ginsenoside Rg1, its metabolites ginsenoside Rh1 and Ppt, and optionally a pharmaceutically acceptable excipient.

In the present invention, the phrase "improving sexual function of male mammals" refers to increasing frequency of sexual behaviour and shortening latent period of sexual behaviour of males. In concrete, the action mechanism of improving sexual function of male mammals resides in increasing content of testosterone in serum of male mammals, and increasing content of cGMP in corpus cavernosum.

In still another aspect, the present invention relates to a method for improving sexual function and/or spermatogenesis of male mammals, comprising administering to a subject a therapeutically effective amount of at least one active ingredient selected from ginsenoside Rg1, its metabolites ginsenoside Rh1 and Ppt. In the present invention, the term "the effect of spermatogenesis" includes promoting spermatogenesis, increasing number of sperms, and/or improving quality of sperms.

EXAMPLE 1

Effect of Ginsenoside Rg1, its Metabolites Ginsenoside Rh1 and/or Ppt on Improving Sexual Function of Mice 1.1.1 Material and Method
1.1.1.1 Animals for Test Kunming male mice (age 10 weeks, weight body 32-36 g), Kunming female mice (age 10 weeks, weight body 30-34 g), as purchased from Laboratory Animal Center of Chinese Academy of Medical Sciences (with the number of certificate SCXK (Jing) 2005-0004), were placed in a clean grade animal house alternately in light and in darkness (12 h:12 h), while taking water and food freely. The test started after the mice had adapted to the environment in the animal house for 5 days. During the period of adapting to the environment, male mice and female mice were isolated from each other.

1.1.1.2 Preparation of Estral Female Mice

In order to correctly reflect the change of male mice in sexual function, we prepared estral female mice by ectomizing their ovaries and inducing them by application of external hormone. After anesthetized with chloral hydrate, female mice were subjected to the steps of ectomizing bilateral ovaries by dorsal approach, ligating uterine tube residue end, and suturing skin, followed by recuperating for one week. The induction by application of hormone was conducted by reference to the literature (Masayoshi Nomura, et al, Physiology & Behavior 91 (2007) 223-228), comprising the steps of subcutaneously injecting estradiol benzoate (30 µg per mouse, is) at 48 h prior to use, and subcutaneously injecting progesterone (500 µg per mouse, is) at 4 h prior to use, to thereby obtain estral female mice.

1.1.1.3 Selection of Male Mice

Estral female mice were put in a ratio of 2:1 to male mice inside a mating box in which male mice were placed. They were trained for consecutive 5 days, 12 min each day. When the mating reaction of male mice became stable, the mice were grouped with the consideration that the bestriding time in each group of mice was substantially the same, while discarding the mice that had relatively weak reaction and no reaction.

1.1.1.4 Test of Sexual Ethology

In darkness, ethological test was carried out in the rearing cage of male mice. Estral female mice and male mice were kept in a ratio of 2:1 inside the same box for 12 min, during which period the bestriding time and mating frequency of the male mice were observed.

1.1.2 Statistic Analysis

All of the values were expressed by using mean value and standard error (M±SEM), the analytic method used was one-way analysis of variance (ANOVA), and the statistic results were expressed by double star method, i.e., *<0.05, **<0.01.

1.1.3 Results 1.1.3.1 Influence of Ginsenoside Rg1, its Metabolites Ginsenoside Rh1 and/or Ppt on Bestriding Time of Mice As can be seen from Table 1, at the $16^{th}$ or $18^{th}$ day after administration, ginsenoside Rg1 and its metabolites ginsenoside Rh1 and/or Ppt, as compared with the control group, all could markedly prolong the bestriding time of mice, without statistic difference among three of Rg1, Rh1 and Ppt. *P<0.05 vs the control group.

TABLE 1

Influence of ginsenoside Rg1, its metabolites ginsenoside Rh1 and/or Ppt on bestriding time of mice (min) (n = 7-8)

| Time | Control | Rg1 (5 mg/kg) | Rg1 (10 mg/kg) | Rh1 (5 mg/kg) | Rh1 (10 mg/kg) | Ppt (5 mg/kg) | Ppt (10 mg/kg) |
|---|---|---|---|---|---|---|---|
| $1^{st}$ day | 2.9 ± 3.2 | 3.1 ± 4.3 | 3.3 ± 2.3 | 2.8 ± 3.2 | 3.6 ± 2.7 | 3.3 ± 2.3 | 2.9 ± 3.4 |
| $4^{th}$ day | 3.6 ± 4.3 | 2.9 ± 3.4 | 3.5 ± 3.1 | 3.5 ± 4.1 | 3.9 ± 3.8 | 3.9 ± 4.2 | 3.3 ± 4.1 |
| $8^{th}$ day | 4.2 ± 3.6 | 3.9 ± 3.1 | 4.2 ± 3.6 | 4.1 ± 3.5 | 4.0 ± 3.5 | 4.5 ± 3.8 | 5.1 ± 3.8 |
| $12^{th}$ day | 5.3 ± 5.4 | 7.6 ± 4.1 | 8.6 ± 4.3 | 6.2 ± 2.9 | 6.3 ± 2.6 | 6.8 ± 3.3 | 7.2 ± 3.3 |
| $14^{th}$ day | 5.2 ± 5.6 | 6.9 ± 3.5 | 7.9 ± 3.7 | 8.6 ± 5.2 | 8.4 ± 3.1 | 7.9 ± 4.4 | 8.4 ± 4.2 |
| $16^{th}$ day | 5.4 ± 4.8 | 8.6 ± 2.8 | 9.2 ± 3.6 | 8.7 ± 4.2* | 8.9 ± 3.7* | 8.3 ± 3.1* | 9.4 ± 3.9* |
| $18^{th}$ day | 5.3 ± 5.5 | 9.4 ± 3.7* | 9.3 ± 3.6* | 8.9 ± 3.3* | 9.1 ± 3.8* | 9.2 ± 3.8* | 9.4 ± 3.9* |
| $20^{th}$ day | 4.2 ± 3.1 | 9.5 ± 3.4* | 9.8 ± 3.8* | 9.2 ± 3.4* | 9.3 ± 3.8* | 9.1 ± 3.5* | 9.4 ± 3.1* |

1.1.3.2 Influence of Ginsenoside Rg1, its Metabolites Ginsenoside Rh1 and/or Ppt on Mating Frequency of Mice As can be seen from Table 2, at the $18^{th}$ day after administration, ginsenoside Rg1 and its metabolites ginsenoside Rh1 and/or Ppt all could markedly increase the mating frequency of mice, without statistic difference among three of Rg1, Rh1 and Ppt. *P<0.05 vs the control group.

TABLE 2

Influence of ginsenoside Rg1, its metabolites ginsenoside Rh1 and/or Ppt on mating frequency of mice (n = 7-8)

| Time | Control | Rg1 (5 mg/kg) | Rg1 (10 mg/kg) | Rh1 (5 mg/kg) | Rh1 (10 mg/kg) | Ppt (5 mg/kg) | Ppt 10 mg/kg |
|---|---|---|---|---|---|---|---|
| $1^{st}$ day | 12.4 ± 7.3 | 15.4 ± 6.4 | 13.8 ± 3.4 | 11.3 ± 4.9 | 9.7 ± 5.6 | 11.4 ± 6.8 | 13.4 ± 6.3 |
| $4^{th}$ day | 17.3 ± 8.3 | 18.7 ± 4.2 | 20.1 ± 4.8 | 13.9 ± 3.3 | 14.3 ± 9.5 | 15.4 ± 8.2 | 15.4 ± 8.4 |
| $8^{th}$ day | 22.4 ± 6.8 | 25.6 ± 5.2 | 28.3 ± 5.6 | 23.5 ± 5.7 | 25.7 ± 8.6 | 27.4 ± 8.7 | 22.8 ± 9.6 |
| $12^{th}$ day | 27.3 ± 8.8 | 32.8 ± 6.6 | 25.3 ± 7.1 | 29.4 ± 4.8 | 28.4 ± 10.5 | 28.2 ± 9.3 | 31.6 ± 8.4 |
| $14^{th}$ day | 25.2 ± 9.3 | 29.3 ± 7.0 | 33.3 ± 6.6 | 33.6 ± 6.1 | 32.2 ± 9.3 | 29.5 ± 7.7 | 33.7 ± 8.5 |
| $16^{th}$ day | 28.4 ± 7.2 | 42.1 ± 10.1 | 37.9 ± 12.7 | 32.2 ± 5.3 | 34.1 ± 8.2 | 33.5 ± 10.4 | 35.3 ± 9.3 |
| $18^{th}$ day | 26.2 ± 9.3 | 43.7 ± 8.7* | 45.1 ± 10.8* | 39.8 ± 9.3* | 36.4 ± 6.7* | 39.2 ± 8.6* | 37.2 ± 8.3* |
| $20^{th}$ day | 22.4 ± 8.9 | 43.3 ± 7.8* | 44.2 ± 9.4* | 38.1 ± 8.5* | 43.4 ± 7.3* | 41.7 ± 7.4* | 40.2 ± 7.3* |

1.1.3.3 Influence of Ginsenoside Rg1 on Content of Testosterone in Serum of Mice After oral administration of ginsenoside Rg1 for 20 days, the content of testosterone in serum of male mice was tested by radioimmune assay. The results demonstrated that ginsenoside Rg1 (10 mg/kg) could markedly increase the content of testosterone in serum. N=6-8. *P<0.05 vs control group (the results were listed in Table 3).

TABLE 3

Influence of ginsenoside Rg1 on content of testosterone in serum of mice

| Group and dose (mg/kg) | content of testosterone (pmol · ml$^{-1}$) |
|---|---|
| Control | 4.20 |
| Rg1 (2.5 mg/kg) | 5.11 |
| Rg1 (5.0 mg/kg) | 5.18 |
| Rg1 (10.0 mg/kg) | 7.90* |

As can be seen from the ethological indexes reflected by the above results, ginsenoside Rg1 and its metabolites ginsenoside Rh1 and/or Ppt all could markedly improve the sexual ethology of mice, and increase the sexuality of mice. It could also be found by the study that both short-term administration and long-term administration could increase the content of testosterone in serum of animals.

Testosterone plays an important role in terms of erection of penis and sexual behavior.

The erection of penis depends on the co-action of stimulation of excitatory signal released by neutral nervous system and pool release of peripheral neurotransmitter. The effectuation of this co-action is just catalyzed by testosterone. That ginsenoside Rg1 and its metabolites ginsenoside Rh1 and/or Ppt can markedly increase the content of testosterone in serum of mice is one of the mechanisms that they improve sexual function of mice.

1.2.1 Influence of Ginsenoside Rg1 on No Release and cGMP Content in Corpus Cavernosum of Newland White Rabbit, as Shown in Table 4

TABLE 4

Influence of ginsenoside Rg1 at different concentrations on NO release and cGMP content in corpus cavernosum of Newland white rabbit

| Group and dose (mg/kg) | NO (µmol/g protein) | cGMP (pmol/g) | n |
|---|---|---|---|
| Control | 21.67 ± 4.69 | 73.08 ± 31.43 | 7 |
| Rg1 (2.5 mg/kg) | 27.97 ± 6.90 | 87.40 ± 42.86 | 7 |
| Rg1 (5.0 mg/kg) | 28.43 ± 6.04* | 98.10 ± 48.40 | 6 |
| Rg1 (10.0 mg/kg) | 30.35 ± 6.70* | 102.73 ± 50.80* | 6 |

As shown in Table 4, ginsenoside Rg1 could increase NO release in corpus cavernosum of rabbit in a dose-dependent manner. The group of ginsenoside Rg1 (5, 10 mg/kg) could significantly increase NO release as compared with the control group, with significant difference between the two groups. Ginsenoside Rg1 (10 mg/kg) could markedly increase cGMP content in corpus cavernosum as compared with the control group. *$P<0.05$ vs the control group.

Ginsenoside Rg1 could not only increase NO release, but also increase cGMP content in corpus cavernosum, to thereby cause erection of penis. In order to further elucidate the mechanism of ginsenoside Rg1 of increasing cGMP content, we tested the cGMP content under the co-action of sodium nitroprusside (NO donor) and ginsenoside Rg1, and observed that, in the case of administering sodium nitroprusside at the same dose, the group of ginsenoside Rg1 still resulted in higher cGMP content than the control group.

It was suggested that ginsenoside Rg1 could prevent the degradation of cGMP by PED5. In order to prove this point, we studied the inhibition effect of ginsenoside Rg1 on PDE5.

1.2.2 Inhibition Effect of Ginsenoside Rg1 on PDE5

TABLE 5

Inhibition effect of ginsenoside Rg1 on PDE5

| Treatment | Inhibitor (nmol/l) | Inhibition rate (%) |
|---|---|---|
| Sildenafil | 2.5 | 71.6 |
|  | 5.0 | 14.6 |
|  | 10.0 | 52.6 |
|  | 20.0 | 83.3 |
|  | 40.0 | 100 |
| Ginsenoside Rg1 | 2.5 | 46.7 |
|  | 5.0 | 40 |
|  | 10.0 | 63.4 |
|  | 40.0 | 100 |
|  | 80.0 | 100 |

Sildenafil $IC_{50}$ = 3.42 nmol
Ginsenoside Rg1 $IC_{50}$ = 4.34 nmol

The cGMP content was tested by using radioimmune autograph technique. The test results demonstrated that ginsenoside Rg1 could block the degradation of cGMP. The increased cGMP content in corpus cavernosum was just caused by the inhibition effect of ginsenoside Rg1 on PDE5. Ginsenoside Rg1 and Sildenafil had no significant difference from each other in terms of the inhibition effect on PDE5.

The effect of ginsenoside Rg1 on improving sexual function of men had been studied in a few of volunteers (healthy men aged 30-50). The results demonstrated that, at the 5$^{th}$ day after administration of ginsenoside Rg1 (100-200 mg/d), the volunteers exhibited significantly improved sexuality, and more frequent erection of penis. Moreover, except for dry mouth, no significant side effects occurred.

EXAMPLE 2

Effect of Ginsenoside Rg1, its Metabolites Ginsenoside Rh1 and/or Ppt on Spermatogenesis 2.1.1 Material and Method 2.1.1.1 Preparation of Medicament Ginsenoside Rg1 and its metabolites ginsenoside Rh1 and/or Ppt were dissolved in water bidistilled, respectively, and stored in an environment of 4° C. Gossypol was provided by Laboratory of Synthesis, Institute of Materia Medica, Chinese Academy of Medical Sciences, dissolved in refined edible oil, and stored in darkness in an environment of 4° C.

2.1.1.2 Animal

Adult Wistar male mice, body weight 180-200 g, as purchased from Laboratory Animal Center of Chinese Academy of Medical Sciences (with the number of certificate SCXK (Jing) 2005-0013).

2.1.1.3 Main Instrument

Computer-assisted sperm assessment (CASA), as developed by Beijing Spaceflight Ruiqi Science and Technology Co., Ltd., and provided by Peking Union Medical College Hospital.

2.1.1.4 Establishment of Aspermatogenesis Model

Mice were orally administered with 50 mg/kg gossypol, once every other day, for two weeks, whereby aspermatogenesis model was established.

2.1.1.5 Grouping of Animals and Dosage Regime

After five days of adapting to the environment, the animals were randomly divided into 8 groups as follows:

Control group: oral administration of edible oil every other day.

Model group: oral administration of 50 mg/kg gossypol every other day.

Groups of Ginsenoside Rg1

Low dose group: administration of 50 mg/kg gossypol every other day, and administration of 5 mg/kg ginsenoside Rg1 every day.

High dose group: administration of 50 mg/kg gossypol every other day, and administration of 10 mg/kg ginsenoside Rg1 every day.

Groups of Metabolite Rh1

Low dose group: administration of 50 mg/kg gossypol every other day, and administration of 5 mg/kg metabolite Rh1 every day.

High dose group: administration of 50 mg/kg gossypol every other day, and administration of 10 mg/kg metabolite Rh1 every day.

Groups of Metabolite Ppt

Low dose group: administration of 50 mg/kg gossypol every other day, and administration of 5 mg/kg metabolite Ppt every day.

High dose group: administration of 50 mg/kg gossypol every other day, and administration of 10 mg/kg metabolite Ppt every day.

At the 14$^{th}$ day, the mice were anesthetized and fixed. Sperms were taken from their tail of epididymis, dissolved in 3 ml physiological saline, and incubated at 37° C. for 5 min. Then, the quality of the sperms was tested by computer-assisted sperm assessment (CASA).

2.1.2 Statistic Analysis

The test results were expressed as x̄±s; the statistic analysis was carried out by t-test to thereby make a comparison among various groups, with $P<0.05$ as an index of significant difference.

2.1.3 Test Results 2.1.3.1 Influence of Ginsenoside Rg1 and its Metabolites Ginsenoside Rh1 and Ppt on Sperm Count in Tail of Epididymis of Mice, as Shown in Table 6

TABLE 6

Influence of ginsenoside Rg1 and its metabolites ginsenoside Rh1 and Ppt on sperm count in tail of epididymis of mice

| Groups | Number of sperms ($10^6 \cdot ml-1$) | Viability rate (%) | Motility of sperms (A + B) (%) |
|---|---|---|---|
| Control | 145 ± 18** | 53 ± 7* | 40 ± 8** |
| Model | 108 ± 25** | 41 ± 8 | 24 ± 3 |
| Rg1 (5 mg/kg) | 170 ± 36**# | 50 ± 10* | 28 ± 6 |
| Rg1 (10 mg/kg) | 225 ± 36**## | 61 ± 9** | 45 ± 8** |
| Rh1 (5 mg/kg) | 142 ± 24** | 56 ± 10** | 39 ± 8** |
| Rh1 (10 mg/kg) | 143 ± 16** | 52 ± 5** | 39 ± 6** |
| Ppt(5 mg/kg) | 141 ± 18** | 55 ± 9** | 38 ± 11* |
| Ppt10 mg/kg) | 178 ± 54** | 56 ± 7** | 39 ± 9** |

The results in Table 6 demonstrated that ginsenoside Rg1 and its metabolites ginsenoside Rh1 and Ppt all could improve the reduced quality of sperms caused by gossypol, with significant difference between the administration groups and the model group. *$P<0.05$ vs model group, **$P<0.01$ vs model group, # $P<0.05$ vs control group, ## $P<0.01$ vs control group.

(attached: WHO standard for classifying motility of sperms: A grade—sperms which move forward quickly; B grade—sperms which move forward slowly or dully; C grade—sperms which do not move forward; D grade—sperms which are immovable).

2.1.3.4 Influence of Ginsenoside Rg1 on No Content in Testis Tissue of Mice

The test was conducted by using a NO kit as established in Nanjing, with the results shown in Table 7.

TABLE 7

Influence of ginsenoside Rg1 on NO content in testis tissue of mice

| Groups | Treatment | NO concentration (μmol/g protein) |
|---|---|---|
| Control | Oil | 9 ± 6** |
| Model | Gossypol | 20 ± 9 |
| Ginsenoside Rg1 | 5 mg/kg | 16 ± 9 |
|  | 10 mg/kg | 10 ± 7** |

As shown in Table 7, NO content in testis of mice in model group was significantly increased as compared with that in control group ($P<0.05$). There was no difference between low-dose group and high-dose group. It was exhibited that NO content in testis of mice in high-dose group was significantly reduced, thus ginsenoside Rg1 could lower NO content in testis, and accordingly could protect sperms. The values were expressed as mean value±SD. **$P<0.01$ vs. model group, n=10.

2.1.3.5 Influence of Ginsenoside Rg1 on Hormones (T, FSH, and LH) Content in Serum of Mice The test was conducted by radioimmune assay, with the use of a kit as purchased from China North Institute of Biological Technology. The results were shown in Table 8.

TABLE 8

Influence of ginsenoside Rg1 on hormones content in serum of mice

| Groups | Treatment | T (ng/ml) | FSH (ng/ml) | LH (ng/ml) |
|---|---|---|---|---|
| Control | Oil | 1.2 ± 0.5** | 5.3 ± 0.9 | 2.7 ± 0.9 |
| Model | Gossypol | 0.3 ± 0.1 | 5.3 ± 0.8 | 2.3 ± 0.4 |
| Ginsenoside Rg1 | 5 mg/kg | 0.8 ± 0.3* | 5.7 ± 2.0 | 2.9 ± 1.2 |
|  | 10 mg/kg | 1.0 ± 0.5** | 4.3 ± 1.9 | 2.1 ± 0.8 |

The above results demonstrated that: testosterone content in serum of mice in model group was significantly reduced as compared with that in control group. The administration of ginsenoside Rg1 (5, 10 mg/kg) could significantly increase testosterone content in serum of mice. The contents of FSH and LH had no significant difference among various groups ($P>0.05$), which suggested that ginsenoside Rg1 directly acted on testis tissue in the model, rather than acting by means of neuroendocrine route. *$P<0.05$ vs. model group, **$P<0.01$ vs. model group, n=10.

EXAMPLE 3

Effect of Ginsenoside Rg1 for Improving Reduced Quality of Sperms in Senile Mice It was proved by the following test that ginsenoside Rg1 had the effect of improving reduced quality of sperms in senile mice. In the test, Kunming mice aged 12 months were used. Ginsenoside Rg1 was orally administered at a dose of 5 mg/kg, once every day, for two weeks. The quality of sperms was still determined by CASA, with the results shown in Table 9.

TABLE 9

Effect of ginsenoside Rg1 for improving reduced quality of sperms in senile mice

| Groups | Treatment | Sperm count (×$10^6$) | Motility sperms (%) | A + B grade (%) |
|---|---|---|---|---|
| Senile mice | DDW | 52.28 ± 32.31 | 50.98 ± 4.95 | 16.54 ± 9.55 |
| Senile mice + ginsenoside Rg1 | 5 mg/kg | 133.23 ± 15.99** | 40 ± 6.56 | 18.27 ± 8.37 |

The above results demonstrated that: the sperm count in the group of senile mice was significantly reduced as compared with that in the group of senile mice+ginsenoside Rg1. However, the two groups had no difference in terms of the percentage of motility sperms and the percentage of A+B grade. It suggested that ginsenoside Rg1 could improve spermatogenesis in senile mice. The values were expressed as mean value±SD. **$P<0.01$ vs. the group of senile mice, n=4.

EXAMPLE 4

Effect of Ginsenoside Rg1 for Improving Reduced Quality of Sperms in Mice in the Condition of Cold Stress It was proved by the following test that ginsenoside Rg1 could improve reduced quality of sperms in mice, which reduced quality of sperms results from cold stress. In the test, Kunming mice were used to establish a stress model. The mice were placed in an environment of 4° C. for 8 hours every day, each being kept in a single cage, with fasting and without water, for 14 days, to thereby establish a cold stress model. Ginsenoside Rg1 was administered at two different doses, i.e., 5 mg/kg and 10 mg/kg. Every day, the mice orally took the drug 1 hour before exposure in the cold environment.

After 14 days, the quality of sperms was determined by CASA, with the results shown in Table 10.

TABLE 10

Effect of ginsenoside Rg1 for improving reduced quality of sperms in mice due to cold stress

| Groups | Treatment | Sperm count (×10⁶) | Motility sperm (%) | A + B grade (%) |
|---|---|---|---|---|
| Control | Water bidistilled | 475.76 ± 98.58 | 54.57 ± 6.15** | 39.36 ± 7.91** |
| Model | Water bidistilled | 454.09 ± 137.30 | 38.91 ± 8.7 | 25.71 ± 10.58 |
| Ginsenoside Rg1 | 5 mg/kg | 438.70 ± 94.19 | 54.47 ± 8.14** | 39.26 ± 8.96** |
| | 10 mg/kg | 377.17 ± 42.93 | 44.97 ± 12.07 | 32.89 ± 13.42 |

The above results demonstrated that repetitive cold stress could reduce the motility of sperms, and ginsenoside Rg1 at 5 mg/kg could improve the quality of sperms, increase the number of motility sperms, and reduce dead sperms.

The above examples demonstrated that the course of spermatogenesis was mainly regulated by hormone as secreted by hypothalamus-pituitary-testis. Among various factors other than hormone, nitric oxide (NO) had become one of the important substances that influence spermatogenesis and capacitation, it took a dual regulating function in terms of spermatogenesis, i.e., a low concentration of NO could stimulate spermatogenesis and capacitation, and increase motility of sperms; while a high concentration of NO could suppress spermatogenesis and motility of sperms. The study has verified that ginsenoside Rg1 could reduce the excess generation of NO caused by gossypol, to thereby improve the reduced quality of sperms induced by gossypol. In addition, ginsenoside Rg1 could significantly improve the reduced quality of sperms due to senile and stress.

The invention claimed is:

1. A method for improving sexual function in a male mammal in need thereof, comprising administering to the male mammal a therapeutically effective amount of a pharmaceutical composition comprising ginsenoside Rg1, ginsenoside Rh1, and ginsenoside 20S-protopanaxatriol (ginsenoside Ppt).

2. The method according to claim 1, wherein said improving sexual function in a male mammal comprises increasing frequency of sexual behaviour or shortening latent period of sexual behaviour.

3. The method according to claim 2, wherein said improving sexual function in a male mammal comprises increasing frequency of sexual behaviour.

4. The method according to claim 2, wherein said improving sexual function in a male mammal comprises shortening latent period of sexual behaviour.

5. A method for increasing content of testosterone in serum or increasing content of cGMP in corpus cavernosum in a male mammal in need thereof, comprising administering to the male mammal a therapeutically effective amount of a pharmaceutical composition comprising ginsenoside Rg1, ginsenoside Rh1, and ginsenoside 20S-protopanaxatriol (ginsenoside Ppt).

6. The method according to claim 5, wherein the method is for increasing content of testosterone in serum.

7. The method according to claim 5, wherein the method is for increasing content of cGMP in corpus cavernosum.

8. A method for promoting spermatogenesis, increasing number of sperms, or improving quality of sperms in a male mammal in need thereof, comprising administering to the male mammal a therapeutically effective amount of a pharmaceutical composition comprising ginsenoside Rg1, ginsenoside Rh1, and ginsenoside 20S-protopanaxatriol (ginsenoside Ppt).

9. The method according to claim 8, wherein the effect of spermatogenesis comprises promoting spermatogenesis.

10. The method according to claim 8, wherein the effect of spermatogenesis comprises increasing number of sperms.

11. The method according to claim 8, wherein the effect of spermatogenesis comprises improving quality of sperms.

12. A method for promoting spermatogenesis, increasing number of sperms, or improving quality of sperms in a male mammal in need thereof, comprising administering to the male mammal a therapeutically effective amount of an active ingredient selected from the group consisting of ginsenoside Rg1, ginsenoside Rh1, and ginsenoside 20S-protopanaxatriol (ginsenoside Ppt).

13. The method according to claim 12, wherein the effect of spermatogenesis comprises promoting spermatogenesis.

14. The method according to claim 12, wherein the effect of spermatogenesis comprises increasing number of sperms.

15. The method according to claim 12, wherein the effect of spermatogenesis comprises improving quality of sperms.

16. A method for treating impotence, treating male sterility, and improving the number and quality of sperms in a male mammal in need thereof, comprising administering to the male mammal a therapeutically effective amount of a pharmaceutical composition comprising ginsenoside Rg1, ginsenoside Rh1, and ginsenoside 20S-protopanaxatriol (ginsenoside Ppt).

17. A method for treating sterility in a male mammal in need thereof, comprising administering to the male mammal a therapeutically effective amount of an active ingredient selected from the group consisting of ginsenoside Rg1, ginsenoside Rh1, and ginsenoside 20S-protopanaxatriol (ginsenoside Ppt).

18. A pharmaceutical composition comprising therapeutically effective amounts of ginsenoside Rg1, ginsenoside Rh1, and ginsenoside 20S-protopanaxatriol (ginsenoside Ppt), and a pharmaceutically acceptable excipient.

* * * * *

UNITED STATES PATENT AND TRADEMARK OFFICE
CERTIFICATE OF CORRECTION

PATENT NO. : 8,765,695 B2  
APPLICATION NO. : 12/530970  
DATED : July 1, 2014  
INVENTOR(S) : Juntian Zhang et al.

Page 1 of 1

It is certified that error appears in the above-identified patent and that said Letters Patent is hereby corrected as shown below:

On the Title Page

Left column, before item (51), insert a new item as follows:

-- (30)  Foreign Application Priority Data

March 12, 2007   (CN)          2007 10064326.0 --.

Signed and Sealed this
Thirtieth Day of December, 2014

Michelle K. Lee
*Deputy Director of the United States Patent and Trademark Office*